Oct. 14, 1969 B. F. McLUCAS Plant Pat. 2,931
PEACH TREE
Filed Aug. 14, 1968
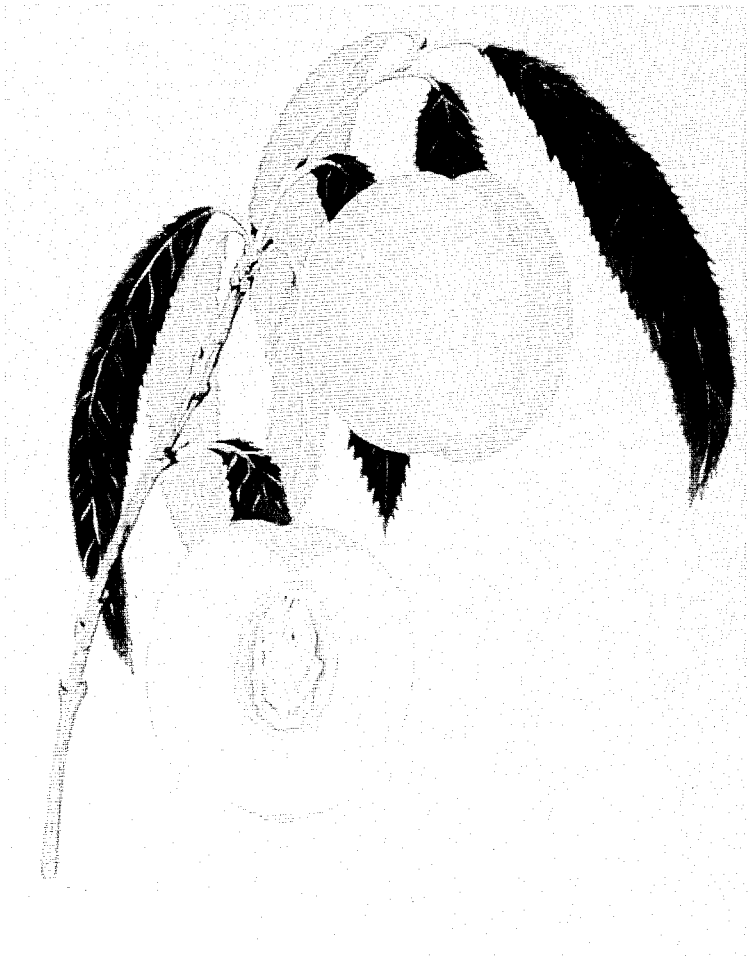

United States Patent Office

Plant Pat. 2,931
Patented Oct. 14, 1969

2,931

PEACH TREE

Ben F. McLucas, 5256 W. Anthony Road, Ocala, Fla. 32670

Filed Aug. 14, 1968, Ser. No. 752,725
Int. Cl. A01h *5/08*
U.S. Cl. Plt.—43 1 Claim

This invention relates to a new and distinct variety of peach tree bearing fruit having yellow with slightly red flesh and being particularly characterized by its low chilling requirement.

The primary object of this invention was to produce a variety of peach tree adapted for growth in central Florida where the January mean temperature ranges from 58 to 62 degrees Fahrenheit and where only about 200 hours of below 45° F. occurs during the tree's dormant season. This chilling requirement of 200 hours below 45° F. is slightly below that of "Flordasun" (unpatented) introduced by the Florida Agricultural Experiment Station.

The peach tree of this invention was originated in the Ocala region of Florida in the following manner. An unnamed seedling selection was obtained from south Georgia and cross by "Jewel" (unpatented, an old Florida peach of the Chinese honey type), seeds from this hybrid were planted and grown to maturity, seeds were obtained from the best of this lot of seedlings and another generation grown to maturity. In the third generation pollen from a seedling selection of progeny was used for hybridization on "L8–112" an unpatented breeding line (Southland × Hawaiian F–2) obtained from the Florida Agricultural Experiment Station. This hybrid fruited in 1963 and trees were budded from it. The fruit and tree characteristics proved to be identical to that of the hybrid tree which fruited in 1963.

As the result of the above, a peach tree having the characteristics sought has been developed. The important bred peach tree are as follows:

(1) A very low chilling requirement of about 200 hours below 45° F.;

(2) Fruit has excellent shipping firmness;

(3) Early ripening of fruit with a picking date of May 7th to 12th in central Florida; late bloom picked about May 21st to 25th;

(4) Very large fruit size for a peach that can be shipped at this time of year;

(5) Much higher coloring at shipping stage than other varieties having similar chilling requirements and season.

A sexual reproduction of this new variety of peach tree in central Florida shows that the above characteristics are established and transmitted through succeeding propagations.

The accompanying color drawing shows leaf and fruit characteristics of the peach of this invention, the fruit being at shipping ripe stage. In addition, a fruit of the subject variety is shown divided at the suture plane to show flesh color and the characteristics of the pit.

The following is a detailed description of this new variety of peach tree, the color designations and terminology being in accordance with Nickerson's Color Fan published by Munsell Color Company.

TREE

Size: Medium large.
Shape: Dense and upright, base formed by pruning.

Trunk: Stocky.
Growth: Vigorous, bears well and regularly commencing at two years old.

LEAVES

Size: 5 to 7 inches long; 1 to 1¼ inches wide on mid-sheet leaves.
Form: Lanceolate, tip acuminate, medium thick.
Color: Upper surface, near moderate olive green (Plate 7.5GY 4/4) underside has moderate yellow green (Plate 7.5GY 5/7), Heavy midrib strong yellow green (Plate 2.5GY 6/8).
Margin: Glandular crenate.
Petiole: ⅜ to ½ inch long on mid-sheet leaves moderately thick.
Stipules: Fall off early.
Glands: 2 to 6, average 4, large reniform type, greenish with few reddish on older leaves.
Buds: Heavy bud set.
Flowers:
*Blooming period.*—Late January in central Florida.
*Quantity.*—Profuse.
*Size.*—Medium-large.
*Color.*—Showy pink petals that turn deep pink at base just before petals fall. Pollen abundant, foiliage well advanced at time of bloom.

FRUIT

Ripening period: Early, ripens in about 97 days from date of bloom, picking date about May 7–12 in central Florida.
Size: 2 to 2½ inches.
Form: Nearly round.
Suture: Distinct raised, has slight depression near pistil point.
Base: Rounded.
Apex: Short.
Stem: Short length ¼ to 5/16 inch, diameter ⅛ inch.
Skin:
*Thickness.*—Medium.
*Tenderness.*—Medium.
*Color.*—Highly colored blush extending over 90% of surface at shipping stage, ranging from strong red (Plate 5R 4/12) to dark red (Plate 2.5R 3/7), under color brilliant yellow green (Plate 2.5GY 8/9) at shipping stage.
*Down.*—Medium. Skin tenacious to flesh when firm ripe, free when soft ripe, no tendency to crack.
Flesh:
*Color.*—Near moderate orange yellow (Plate 10YR 8/10) very little red near pit, flecks of red halfway between pit and outer surface at shipping stage, at ripe stage these flecks of red become very pronounced and change to solid streaks of red.
*Texture.*—Firm with no fibers, ripens evenly.
*Flavor.*—Moderately acid, mild, good blend of sweetness and acidity.
*Quality.*—Good.
Stone: Semi-cling, near free when ripe.
*Size.*—1 to 1¼ inches long, ⅞ to 1 inch wide, ⅝ to 11/16 inches thick.
*Form.*—Obovate.
*Base.*—Oblique.

*Apex.*—Short acuminate.
*Surface.*—Irregularly furrowed and pitted.
*Color.*—Brownish orange (Plate 5YR 5/8).
Shipping quality: Very good.
Keeping quality: Very good.
Use: Excellent for table use.

I claim:

1. A new and distinct variety of peach tree of the yellow fleshed with slight red coloring, semi-freestone fruit bearing type substantially as herein shown and described, characterized particularly by its uniqueness of low chilling requirement of 200 hours of winter chilling below 45° F. thereby making it suitable for growth in central and south central Florida, further characterized by its heavy bearing qualities at the early age of two years, its very large fruit of excellent color and firmness of an early ripening variety, and its early ripening of approximately 97 days from date of bloom to shipping ripe stage with a picking date of May 7 to 12 in central Florida.

No references cited.

ROBERT E. BAGWILL, Primary Examiner